(12) United States Patent
Park

(10) Patent No.: US 9,636,289 B2
(45) Date of Patent: May 2, 2017

(54) COMPOSITION FOR PREVENTING OR TREATING HAIR LOSS OR PROMOTING HAIR GROWTH COMPRISING SECOIRIDOID GLUCOSIDE DERIVATIVES

(71) Applicant: INDUSTRY-ACADEMIC COOPERATION FOUNDATION, YONSEI UNIVERSITY, Seoul (KR)

(72) Inventor: Tae Sun Park, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/356,162

(22) PCT Filed: Jul. 8, 2013

(86) PCT No.: PCT/KR2013/006061
§ 371 (c)(1),
(2) Date: May 4, 2014

(87) PCT Pub. No.: WO2014/010900
PCT Pub. Date: Jan. 16, 2014

(65) Prior Publication Data
US 2015/0119347 A1    Apr. 30, 2015

(30) Foreign Application Priority Data
Jul. 9, 2012 (KR) .................... 10-2012-0074407

(51) Int. Cl.
*A61K 8/60* (2006.01)
*A61Q 7/00* (2006.01)
*A61K 31/7048* (2006.01)

(52) U.S. Cl.
CPC .......... *A61K 8/602* (2013.01); *A61K 31/7048* (2013.01); *A61Q 7/00* (2013.01)

(58) Field of Classification Search
None
See application file for complete search history.

(56) References Cited

U.S. PATENT DOCUMENTS

| | | | | |
|---|---|---|---|---|
| 4,828,837 A | * | 5/1989 | Uster | ........... A61K 8/14 264/4.1 |
| 4,996,057 A | * | 2/1991 | Schoeff | ........... A61K 8/41 424/583 |
| 2003/0004117 A1 | * | 1/2003 | Hamdi | ........... A61K 31/23 514/25 |
| 2003/0170331 A1 | * | 9/2003 | Cals-Grierson et al. | ..... 424/769 |
| 2007/0184003 A1 | * | 8/2007 | Gaunitz | ........... 424/70.11 |
| 2011/0217260 A1 | * | 9/2011 | Shantha | ........... A61K 8/28 424/85.2 |

FOREIGN PATENT DOCUMENTS

| | | |
|---|---|---|
| JP | 2005-179353 A | 7/2005 |
| KR | 10-2008-0026017 A | 3/2008 |
| KR | 10-2010-0070665 A | 6/2010 |
| KR | 10-2012-0052894 A | 5/2012 |
| WO | WO 9614064 A1 * | 5/1996 |

OTHER PUBLICATIONS

Durlu-Özkaya, J Food Process Technol vol. 2, Issue 3, 2011.*
International Search Report for PCT/KR2013/006061, Oct. 2013.
Soyoung Park et al, Oleuropein attenuates hepatic steatosis induced by high-fat diet in mice, Journal of Hepatology, 2011, vol. 54, pp. 984-993.

* cited by examiner

*Primary Examiner* — Layla Berry
(74) *Attorney, Agent, or Firm* — Harness, Dickey & Pierce, P.L.C.

(57) ABSTRACT

The present invention provides a method for preventing or treating hair loss or promoting hair growth, comprising secoiridoid glucoside derivatives or hydrolysate thereof as active ingredients. The present invention not only includes natural compounds as an active ingredient without side effects of the long-term treatment in a chronic disease hair loss, but also shows excellent effects for promoting hair growth with stable efficacy. Therefore, the present invention may be used as an effective pharmaceutical, cosmetic or functional food composition for preventing or treating hair loss or promoting hair growth.

2 Claims, 5 Drawing Sheets

COMPOSITION FOR PREVENTING OR TREATING HAIR LOSS OR PROMOTING HAIR GROWTH COMPRISING SECOIRIDOID GLUCOSIDE DERIVATIVES

CROSS-REFERENCE TO RELATED APPLICATIONS

This patent application claims benefit under 35 U.S.C. 119(e), 120, 121, or 365(c), and is a National Stage entry from International Application No. PCT/KR2012/000756, filed Jan. 31, 2012, which claims priority to Korean Patent Application No. 10-2012-0074407, filed on 09 Jul. 2012, in the Korean Intellectual Property Office, the disclosure of which is incorporated herein by reference.

BACKGROUND OF THE INVENTION

Field of the Invention

The present invention relates to a composition and a method for preventing or treating hair loss or promoting hair growth comprising secoiridoid glucoside derivatives.

Description of the Related Art

According to the report of National Health Insurance Corporation from 2001 to 2008, the numbers of patients of 'hair loss diseases' are estimated at 103,000 people in 2001, at 142,000 people in 2005 and at 165,000 people in 2008. It has increased by 60% for seven years. The number of patients in 20s to 40s is estimated at 114,000 people and it is accounted for 69.5% of whole patients. In addition, the number of patients in 10s is estimated at more than 22,000 people. The numbers of patients are estimated at 84,000 people in male, and at 80,000 people in female. The numbers of patients of hair loss disease in 2008 Korean Health Insurance treatment are alopecia areata (130,000 people), cicatricial alopecia (20,000 people), androgenetic alopecia (9,000 people) and other nonscarring hair loss (8,000 people) in order.

In abroad, according to data in June 2003 International Hair and Beauty Studies, hair loss patients are 250 million people, and prevalence rate of hair loss patients between the ages of twenty-four and fifty years old is 30-65%. In China, the number of hair loss patients is 300 million people in 2008. 30% of 30s and 50% of 50s in male show signs of hair loss, and the number of hair loss patients are increased by 10-15% every year. In Japan, prevalence rate of hair loss is 26.5%, and the number of hair loss patients is estimated at 12.93 million people.

Currently, drugs for treating hair loss are classified as pharmaceutical medicines, quasi-drugs and cosmetics. Prescription drug on the doctor's is 'Propecia' developed by Merck (U.S.), and its active ingredient Finasteride has been approved as drugs for treating hair loss from the U.S. FDA in December 1997. Finasteride inhibits 5-a-reductase which converts testosterone to dihydrotestosterone (DHT), whereby it results in growth of thick and long hair. Although it has an effect for alleviating hair loss in the short term, side effects such as impotence, sexual dysfunction and male breast enlargement have been reported. Minoxidil has been recognized as drug available to purchase without a doctor's prescription in safety and efficacy, and it has been firstly approved as spread drugs for treating hair loss from the U.S. FDA in December 1997. It improves blood circulation and opens potassium channels to promote hair growth. However, it has side effects such as itching, rash and frequent pulse.

Quasi-products for hair loss prevention and hair growth functions approved from Korea Food & Drug Administration include 'Mobalryeok confidence (CJ lion)', 'Hair Tonic (Moracle)' and 'Moaenmoah (LG Household & Health Care)'. Products of cosmetics and shampoos have been sold to maintain or promote health of skin and hair.

Hair production occurs in phases, including growth (anagen), cessation (catagen), and rest (telogen) phases. The anagen is the active growth phase of hair follicles during which the root of the hair is diving rapidly, adding to the hair shaft. The life span of hairs in the anagen stage ranges from 3 to 6 years. Hairs in the anagen phase accounts for 80-90% of the entire hair. In hair loss in progress, shorter anagen and longer catagen lead to reduce the proportion of anagen in the entire hair. In catagen stage after anagen stage, the metabolism of hairs becomes to be slower with maintaining the shape of hairs and hair grows slowly. The catagen stage continues for 1-1.5 months and occupies 1% of total hairs. In the telogen phase, hair follicle is gradually contracted, and the hair root is pushed upward to be finally removed. This phase lasts for about 3-4 month, and accounts for 4-14% of total hairs. Lastly, at the new anagen, hair bulbs which is surrounded by hair follicles in the anagen stage, combines with hair papilla to induce the formation of new hairs. Afterwards, the new hairs push upward and naturally remove old hairs in the talogen stage.

Oleuropein contained in large quantities in olive leaf and olive oil is a secoiridoid compound with slightly bitter scent of olive leaf. Oleuropein has a molecular formula of $C_{25}H_{32}O_{13}$ and a molecular weight of 540.514, represented by the following chemical formula:

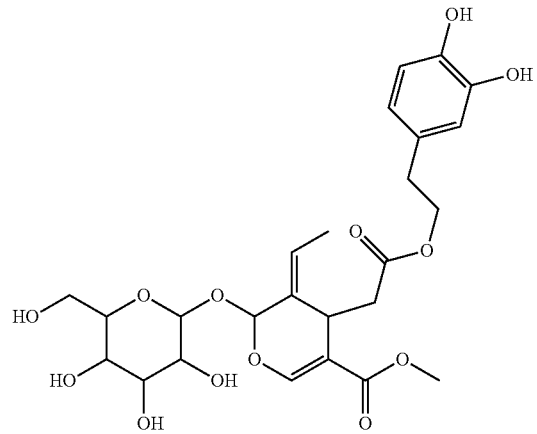

Biological activity of oleuropein is known to be effective in antioxidant, antiviral, anticancer, antibacterial, antiobesity and improvement of non-alcoholic fatty liver. In addition, there is no toxicity of oleuropein in mouse treated with 1 g/kg (body weight) of oleuropein for 7 days, and $LD_{50}$ of oleuropein may not be calculated through various experiments. Therefore, it is suggested that oleuropein is a substance with a significant high safety.

However, the efficacy of oleuropein related to promotion of hair growth or improvement of hair loss has been not known so far.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel compounds or derivatives thereof derived from natural substances having therapeutic efficacies for preventing or treating hair loss or promoting hair growth. As a result, they have found out that secoiridoid glucoside derivatives (e.g., oleuropein) contained in plant belonging to the family Oleaceae simulate hair growth and prevent hair loss with high efficiency through various tests.

Accordingly, it is an object of this invention to provide a pharmaceutical composition for preventing or treating hair loss or promoting hair growth, comprising secoiridoid glucoside derivatives, more specifically oleuropein, or hydrolysate thereof.

It is another object of this invention to provide a cosmetic composition for preventing or treating hair loss or promoting hair growth, comprising secoiridoid glucoside derivatives, more specifically oleuropein, or hydrolysate thereof.

It is still another object of this invention to provide a functional food composition for preventing or treating hair loss or promoting hair growth, comprising secoiridoid glucoside derivatives, more specifically oleuropein, or hydrolysate thereof.

It is further object of this invention to provide a method for preventing or treating hair loss or promoting hair growth, comprising secoiridoid glucoside derivatives, more specifically oleuropein, or hydrolysate thereof.

Other objects and advantages of the present invention will become apparent from the detailed description to follow taken in conjugation with the appended claims and drawings.

DETAILED DESCRIPTION OF THIS INVENTION

Figure 1:
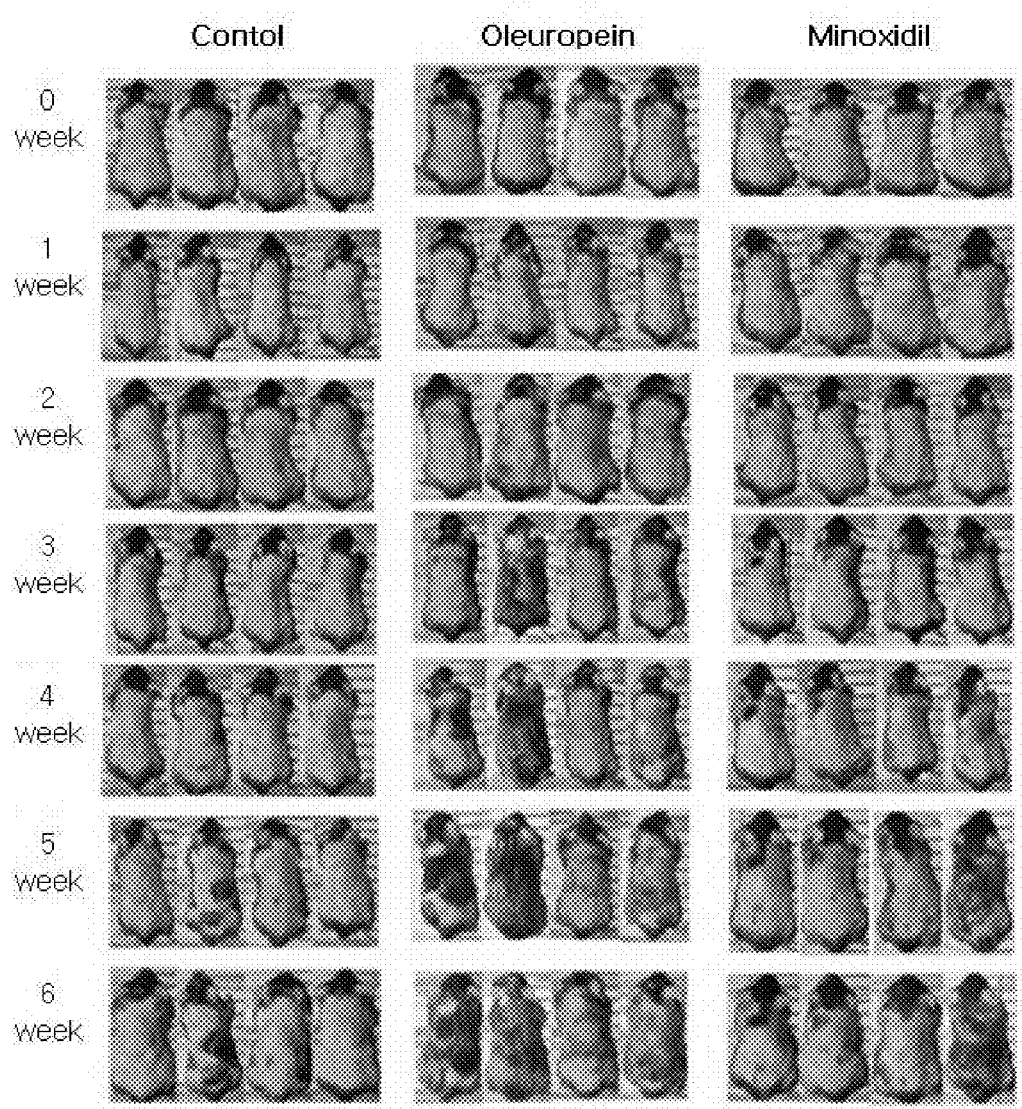
FIG. 1 represents the results on hair re-growth with the lapse of time of hair restorer injection in mouse model removed hair.

In one aspect of the present invention, there is provided a pharmaceutical composition for preventing or treating hair loss or promoting hair growth, comprising administering to a mammalian subject in need thereof a therapeutically effective amount of a composition comprising a secoiridoid glucoside derivative or its hydrolysate represented by the Chemical Formula 1 as an active ingredient:

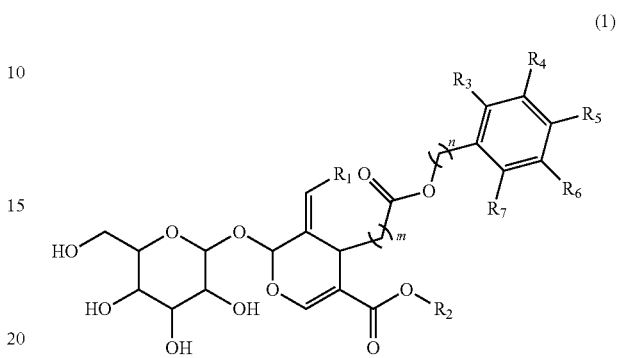

(1)

wherein $R_1$ and $R_2$ is independently $C_1$-$C_4$ alkyl; $R_3$-$R_7$ are independently hydrogen, hydroxy or $C_1$-$C_4$ alkyl; m is an integer of 1 to 3; and n is an integer of 1 to 4.

The present inventors have made intensive researches to develop novel compounds or derivatives thereof derived from natural substances having therapeutic efficacies for preventing or treating hair loss or promoting hair growth. As a result, they have found out that secoiridoid glucoside derivatives (e.g., oleuropein) contained in plant belonging to the family Oleaceae simulate hair growth and prevent hair loss with high efficiency through various tests.

As demonstrated in the following Examples, oleuropein converts hairs of the telogen to hairs of the anagen, and increases the number of hair follicles and expressions of growth factors related hair growth in skin tissue such that ultimately, hair density per unit skin area significantly increased.

Having described efficacies for preventing or treating hair loss or promoting hair growth of oleuropein as representative of secoiridoid glucoside derivatives in Examples, it is apparent to one of skill in the art that secoiridoid glucoside derivatives encompassed by the Chemical Formula 1 and showing similar levels of biological activities to oleuropein may also show similar efficacies to oleuropein for preventing or treating hair loss or promoting hair growth.

In addition, it has been known that elenolic acid, in which glycosyl group of secoiridoid glucoside derivatives is hydrolyzed to form, shows same or similar level of biological activity of oleuropein (U.S. Pat. Nos. 6,117,844 and 6,455,580). This elenolic acid may be also formed when secoiridoid glucoside derivatives are metabolized in vivo. Therefore, it is apparent that hydrolysates of secoiridoid glucoside derivatives may also show similar efficacies to oleuropein for preventing or treating hair loss or promoting hair growth, to those skilled in this art.

There is no intended distinction between the terms used herein "for preventing hair loss," "for treating hair loss," "for improving hair loss," or "for promoting hair growth," and these terms will be used interchangeably. In addition, these terms have the same meaning with the term "promotion of hair growth" used in this art.

The term used herein "alkyl" refers to a saturated hydrocarbon radical, which may be straight or branched. For example, it includes methyl, ethyl, propyl, isobutyl, pentyl or hexyl. $C_1$-$C_4$ alkyl means an alkyl group having an alkyl unit of 1-4 carbon atoms. When the $C_1$-$C_4$ alkyl is substituted, the number of carbons in the substituent is not included.

According to a preferred embodiment, $R_1$ and $R_2$ in the Chemical Formula 1 is independently $C_1$-$C_2$ alkyl; $R_3$-$R_7$ are independently hydrogen or hydroxy; m is 1; and n is 2.

More preferably, the secoiridoid glucoside derivative in the Chemical Formula 1 is a compound represented by the Chemical Formula 2:

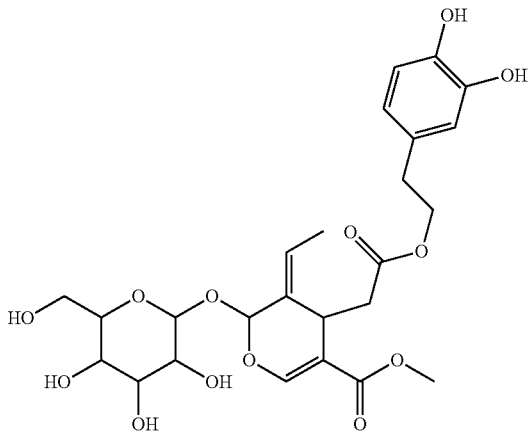 [SMILES: C/C=C1/C(OC2OC(CO)C(O)C(O)C2O)OC=C(C(=O)OC)C1CC(=O)OCCc1ccc(O)c(O)c1]

Chemical Formula 2

According to the present invention, the compound represented by the Chemical Formula 2 is oleuropein.

Plant belonging to the family Oleaceae contains a lot of oleuropein in fruits, roots, stems, particularly, leaves, and includes approximately more than 600 species in 24 of genus.

The plant belonging to the family Oleaceae used in the present invention is not particularly limited as long as it contains secoiridoid glucoside derivative including oleuropein, and preferably olive tree (*Olea europaea*), plant from genus *Ligustrum*, plant from genus *Syringa*, plant from genus *Fraxinus*, plant from genus *Jasminum* or plant from genus *Osmanthus*.

The extract of plant belonging to the family Oleaceae containing secoiridoid glucoside derivative may be obtained using conventional extraction solvents, and preferably the extraction solvent used in this invention includes (a) absolute or hydrous lower alcohol containing 1-4 carbon atoms (e.g., methanol, ethanol, propanol, butanol, n-propanol, isopropanol and n-butanol), (b) mixture of lower alcohol and water, (c) acetone, (d) ethyl acetate, (e) chloroform, (f) 1,3-butyleneglycol, (g) hexane, (h) diethylether, (i) butyl acetate or (j) water.

The fraction of plant belonging to the family Oleaceae containing secoiridoid glucoside derivative refers to a isolated/purificated form obtained by additional separation/purification to the extract of plant belonging to the family Oleaceae. For instance, it could be appreciated that active fractions obtained using a variety of additional purification methods such as an ultrafiltration with defined molecular weight cut-off value and various chromatography (designed for purification dependent upon size, charge, hydrophobicity and affinity) are included in the present extracts.

A method for obtaining oleuropein using *Olea europaea* leaf extract is described accurately in U.S Patent Application Publication No. 2003-0017217.

In addition, the secoiridoid glucoside derivative may be synthesized chemically. A method for synthesizing oleuropein is described accurately in PCT Application Publication NO. WO96/14064.

According to a preferred embodiment, the present composition increases expressions of IGF-1 (Insulin-like growth factor 1), VEGF (vascular endothelial growth factor), HGF (hepatocyte growth factor), KGF (keratocyte growth facfor) or β-catenin.

The present inventors have made various researches to verify that the present composition simulates hair growth in the molecular level. As a result, they have found out that the present composition significantly increases expression levels of β-catenin as well as IGF1, VEGF, HGF and KGF as growth factors which influence on promotion of hair growth, whereby β-catenin signaling pathway is activated. It has been known that β-catenin signaling pathway play a pivotal role in hair follicle generation and hair growth. Therefore, the present composition may be applied to an effective hair restorer composition having various and stable efficacies for promoting hair growth.

According to the present invention, the present composition may be prepared to a pharmaceutical composition for preventing or treating hair loss. When the composition of the present disclosure is prepared as a pharmaceutical composition, the pharmaceutical composition of the present disclosure may comprise a pharmaceutically acceptable carrier. The pharmaceutical composition may contain a pharmaceutically acceptable carrier. In the pharmaceutical compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methyl hydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995), which is incorporated herein by reference.

The pharmaceutical composition of this invention may be preferably administered orally or parenterally, more preferably subcutaneously injection.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Physicians of ordinary skill in the art can determine an effective amount of the pharmaceutical composition for desired treatment. Generally, the pharmaceutical composition of the present invention may be administered with a daily dose of 0.001-100 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. The formulation may be in the form of a solution in oily or aqueous medium, a suspension, a syrup, a emulsion, an extract, an elixir, a powder, a granule, a tablet or a capsule, and may further include a dispersant or stabilizer.

In another aspect of the present invention, there is provided a cosmetic composition for improving hair loss or promoting hair growth, comprising secoiridoid glucoside derivative or its hydrolysate represented by the Chemical Formula 1 as an active ingredient.

Since the secoiridoid glucoside derivative used in the present invention is described as above, the common descriptions between them are omitted in order to avoid undue redundancy leading to the complexity of this Specification.

The present cosmetic composition includes the secoiridoid glucoside derivative or its hydrolysate the Chemical Formula 1 as an active ingredient, and also the components that are generally used in the cosmetic composition, in which the components include for example, general adjurvants, such as an antioxidant, a stabilizer, a dissolving agent, vitamins, pigments, and flavouring, and carriers.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softner, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar or tragacanth.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives or ethoxylated glycerol fatty acid ester.

In still another aspect of the present invention, there is provided a functional food composition for improving hair loss or promoting hair growth, comprising secoiridoid glucoside derivative or its hydrolysate represented by the Chemical Formula 1 as an active ingredient.

Since the secoiridoid glucoside derivative, used in the present invention is described as above, the common descriptions between them are omitted in order to avoid undue redundancy leading to the complexity of this Specification.

When the composition of the present disclosure is prepared as a functional food composition, the food composition of the present disclosure may comprise, in addition to the secoiridoid glucoside derivative or its hydrolysate the Chemical Formula 1 of the present disclosure as the active ingredient, ingredients commonly added for preparation of food. For example, proteins, carbohydrates, fats, nutrients, seasoning or flavors may be added. The carbohydrate may be, for example, a sugar such as a monosaccharide, e.g. glucose, fructose, etc., a disaccharide, e.g. maltose, sucrose, oligosaccharide, etc. or a polysaccharide, e.g. dextrin, cyclodextrin, etc. or a sugar alcohol such as xylitol, sorbitol, erythritol, etc. The flavor may be a natural flavor [thaumatin, stevia extract (e.g. rebaudioside A, glycyrrhizin, etc.)] or a synthetic flavor (saccharin, aspartame, etc.).

For example, when the food composition of the present disclosure is prepared as a drink, it may further comprise, in addition to nonenal of the present disclosure as the active ingredient, citric acid, high-fructose corn syrup, sugar, glucose, acetic acid, malic acid, fruit juice, eucommia extract, jujube extract, licorice extract, or the like.

In further aspect of the present invention, there is provided a method for preventing or treating hair loss or promoting hair growth, comprising administering to a mammalian subject in need thereof a therapeutically effective amount of a composition comprising a secoiridoid glucoside derivative or its hydrolysate represented by the Chemical Formula 1 as an active ingredient:

Since the secoiridoid glucoside derivative used in the present invention is described as above, the common descriptions between them are omitted in order to avoid undue redundancy leading to the complexity of this Specification.

The features and advantages of this invention will be summarized as follows:

(a) The present invention provides a pharmaceutical composition for preventing or treating hair loss, comprising a secoiridoid glucoside derivative or its hydrolysate as an active ingredient. In addition, the present invention provides a cosmetic composition or functional food composition for improving hair loss or promoting hair growth, comprising a secoiridoid glucoside derivative or its hydrolysate as an active ingredient.

(b) The present invention not only includes natural compounds as an active ingredient without side effects of the long-term treatment in a chronic disease hair loss, but also shows excellent effects for simulating hair growth with stable efficacy. Therefore, the present composition may be used as an effective cosmetic or functional food composition for treating hair loss or promoting hair growth.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Efficacy of Oleuropein for Promoting Hair Growth

Animal Model
(1) Preparation of Sample
Corn oil used as the vehicle and minoxidil used as the control group were purchased from Sigma-Aldrich. The test substance oleuropein was purchased from Extrasynthese.
(2) Maintenance of Test Animals
12 of 6-week-old male C57BL/6N mice (Orientbio) were adapted to the environment for 2 weeks. Then, they were divided into total 3 groups, the negative control group (Con), the positive control group (MXD) and oleuropein group (Ole), and used for test. The environment for animals were maintained at 21±2.0° C. and relative humidity 50±5% under 12 hours light/dark cycle. They were fed a food (chow) and water with free access.

(3) Subcutaneous Injection of Hair Restorers and Visual Observation Thereof

In order to verify an effect for promoting hair growth, 8-week-old mice in telogen were used for test. Hairs of their back were removed using a clipper for mouse. They were subcutaneously injected with 0.1 mL of sample at the part, everyday. Before subcutaneous injection, the test substance oleuropein (0.8 mg/0.1 mL) and the control drug minoxidil were dissolved in corn oil to use. The negative control group was subcutaneously injected with only vehicle (corn oil). The application was performed once, every P.M. 4:00 for 6 weeks. At 1 week, 2 weeks, 3 weeks, 4 weeks, 5 weeks and 6 weeks after the application, mice were anaesthetized with ether to take pictures of their back in order to verify hair growth state. To assess level of hair growth, the hair length was measured using ruler.

Measurement on Changes in Body Weight

Figure 2:
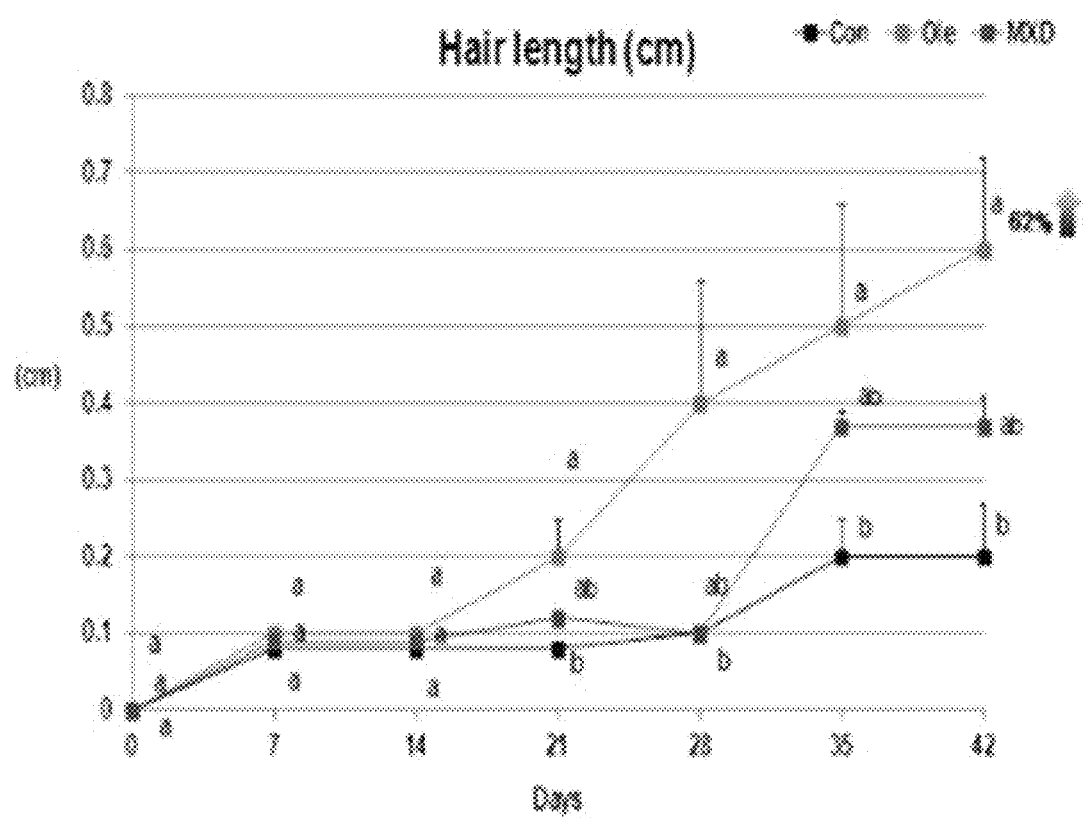
FIG. 2 represents the graph of grown hair length during the experimental period in mouse subcutaneously injected with hair restorers. The results are represented as mean±SEM (standard error) of values obtained from eighty four (84) mice. The characters above the bars indicate significant difference among dietary groups by one-way analysis of variance (ANOVA) test and Duncan's multiple range test ($P<0.05$).

Body weight was measured weekly during entire test period, from the point before the subcutaneous injection of the hair restorers to the end point of the subcutaneous injection of the hair restorers. There are no significant differences between the negative control group (Con), the test group (Ole) and the positive control group (MXD) in the body weights at 6 weeks as well as the initial body weights.

control group MXD and the negative control group in hair length after 4 weeks, although hair length was increased at 5 weeks (FIG. 2). Accordingly, it would be determined that oleuropein has an excellent effect for stimulating hair growth than that of the minoxidil as conventional hair restorer.

Histological Analysis of the Back Skin (1) Histological Method

At 6 weeks after subcutaneous injection, mice were sacrificed. Their back skin tissue samples were isolated using scissors and forceps and fixed by formalin. After dehydration with serial alcohol and xylene, the tissues were paraffinized. Paraffinized tissues were sectioned using a microtomb in a thickness of 5 µm and used alcohol and xylene to remove paraffin. Then, the tissues were stained with hematoxyline/eosin, followed by observation of histological changes in hair follicles under an optical microscope. The hair growth cycles in the tissues were pathologically diagnosed by specialists, and quantity and diameter of hair follicle were measured under an optical microscope.

(2) Histological Analysis

The results as described above are shown in Table 1. All hair growth cycles measured before administration of the test substance (non-treatment) were observed to telogen. Therefore, it would be considered that 8 week-old animals used in the present test were qualified as a model of the hair growth efficacy evaluation. As a result, the anagen phases were observed in the negative group (1 case), the MXD group (1 case) and the Ole group (2 cases), respectively.

TABLE 1

| Histological diagnosis | | | | | | | |
|---|---|---|---|---|---|---|---|
| No treatment | | Corn-oil vehicle | | Oleuropein | | Minoxidil | |
| Animal ID | Diagnosis | Animal ID | Diagnosis | Animal ID | Diagnosis | Animal ID | Diagnosis |
| 1 | Telogen | 1 | Telogen | 1 | Telogen | 1 | Telogen |
| 2 | Telogen | 2 | Anagen | 2 | Telogen | 2 | Telogen |
| 3 | Telogen | 3 | Telogen | 3 | Anagen | 3 | Telogen |
| 4 | Telogen | 4 | Telogen | 4 | Anagen | 4 | Anagen |
| Anagen ratio | 0% | Anagen ratio | 25% | Anagen ratio | 50% | Anagen ratio | 25% |

Measurement on Changes in Hair Growth State and Hair Length.

(1) Visual Characteristics in Hair Growth Mice injected subcutaneously with the samples for 6 weeks were weekly took pictures of their back to verify hair growth state. Body surface of mice in the telogen showed pink color after the hair removal. Body surface color turned to black as the test was carried out, indicating that the telogen returns to the anagen in hair cycle.

In mice injected subcutaneously with corn oil, hairs were rarely grown after 6 weeks. In contrast, in mice injected subcutaneously with oleuropein, hairs were grown at 3 weeks. Moreover, hairs were vigorously grown at 6 weeks. Accordingly, it would be determined that oleuropein has more excellent effect for promoting hair growth than that of the minoxidil (FIG. 1).

(2) Changes in Hair Length

Figure 3:
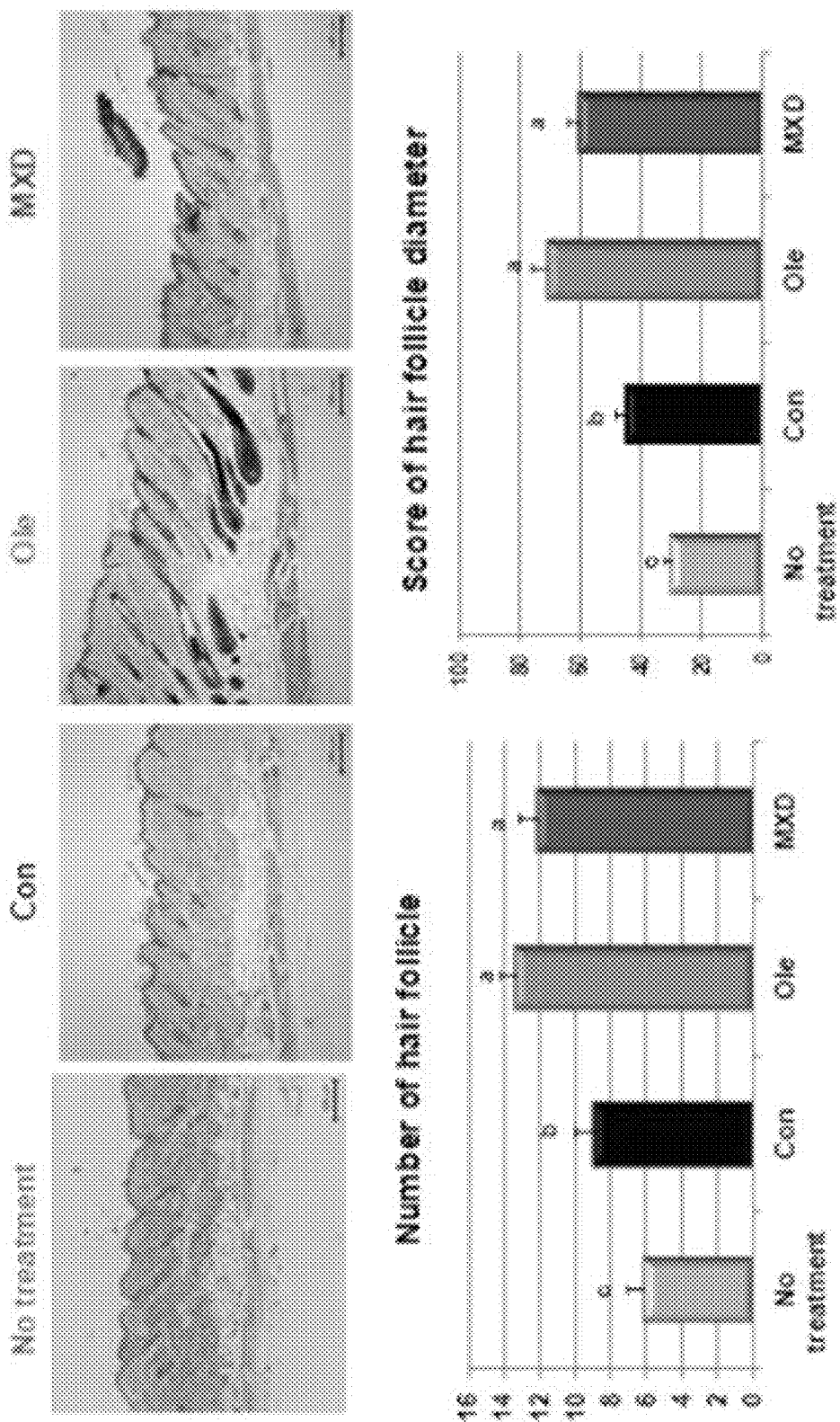
FIG. 3 represents the results on histological analysis in the back skin of mouse subcutaneously injected with hair restorer for 6 weeks. The results are represented as mean±SEM (standard error) of values obtained from four (4) mice. The characters above the bars indicate significant difference among dietary groups by one-way analysis of variance (ANOVA) test and Duncan's multiple range test ($P<0.05$).

Hair length in mice injected subcutaneously with the samples for 6 weeks were weekly measured. In oleuropein group, hair length was significantly increased (p<0.05) at 3 weeks. In addition, it was significantly increased by 62% at 6 weeks, compared to the negative control group. However, there was no significant difference between the positive The measurement results of the number of hair follicles under an optical microscope of 40× magnification are shown in FIG. 3. The number of hair follicles in the Ole group and the MXD group was significantly increased as compared to the negative control group. As a result of image analysis, the diameter of the hair follicles in the Ole group and the MXD group was significantly increased as compared to the negative control group. In addition, there is a phenomenon that hair follicles in the Ole group and the MXD group became longer and they were expressed into skin. It would be considered that this phenomenon is related to effects of the two substances for simulating hair growth.

Example 2

Expression Controls of Hair Growth-Related Genes and Proteins by Oleuropein

Immunohistochemical Test on Skin Tissue (1) Immunohistochemical Method

In order to verify expression amounts of IGF1 and β-catenin related with hair growth in skin tissue, each primary antibody to IGF1 and β-catenin was diluted to 1:50, added to tissue sections, and incubated for 12 hours at room temperature. The primary antibody was diluted with the mixture of 0.1% normal goat serum (Vector Laboratories Inc.) and 0.3% Triton X-100 (Sigma) in 0.1 M phosphate buffer solution (PB). The tissue sections were washed twice at room temperature for 15 minutes in 0.1M PB. Then, secondary antibody [biotinylated anti-rabbit IgG (Vector Laboratories Inc.)] was diluted to 1:200, added to the tissue sections, and incubated for 1 hour at room temperature. The tissue sections were washed twice at room temperature for 15 minutes in 0.1M PB, soaked in peroxidase-labeled ABC solution, and incubated for 1 hour at room temperature. The tissue sections were washed twice at room temperature for 15 minutes in 0.1M PB. Then, the tissue sections were reacted for 5 min with a solution in which 30 mg of 3-3' diaminobenzidine was dissolved in 150 ml of 0.1M PB, added with concentration of 0.005% of hydrogen peroxide, and reacted for 5 min to occur color reaction. The tissue sections were washed several times at room temperature in 0.1M PB. Then, according to the conventional methods, the tissues were counterstained with hematoxyline for 20 sec, dehydrated, transparentized and mounted, followed by observation under an optical microscope.

(2) Immunohistochemical Analysis

It has been identified that intracellular signaling active factors such as Wnt/β-catenin, in addition to male hormones and growth hormones, play a role in hair growth and loss. In the development of drugs for inhibiting hair loss and simulating hair growth, screening for efficacies of the Wnt/β-catenin signaling molecules as target have been researched. In the present invention, the present inventors have made intensive researches to develop substances for activating Wnt/β-catenin signaling which is known to play a pivotal role in hair follicle generation and hair growth, and to apply as a material of products for inhibiting hair loss and simulating hair growth.

Figure 4:
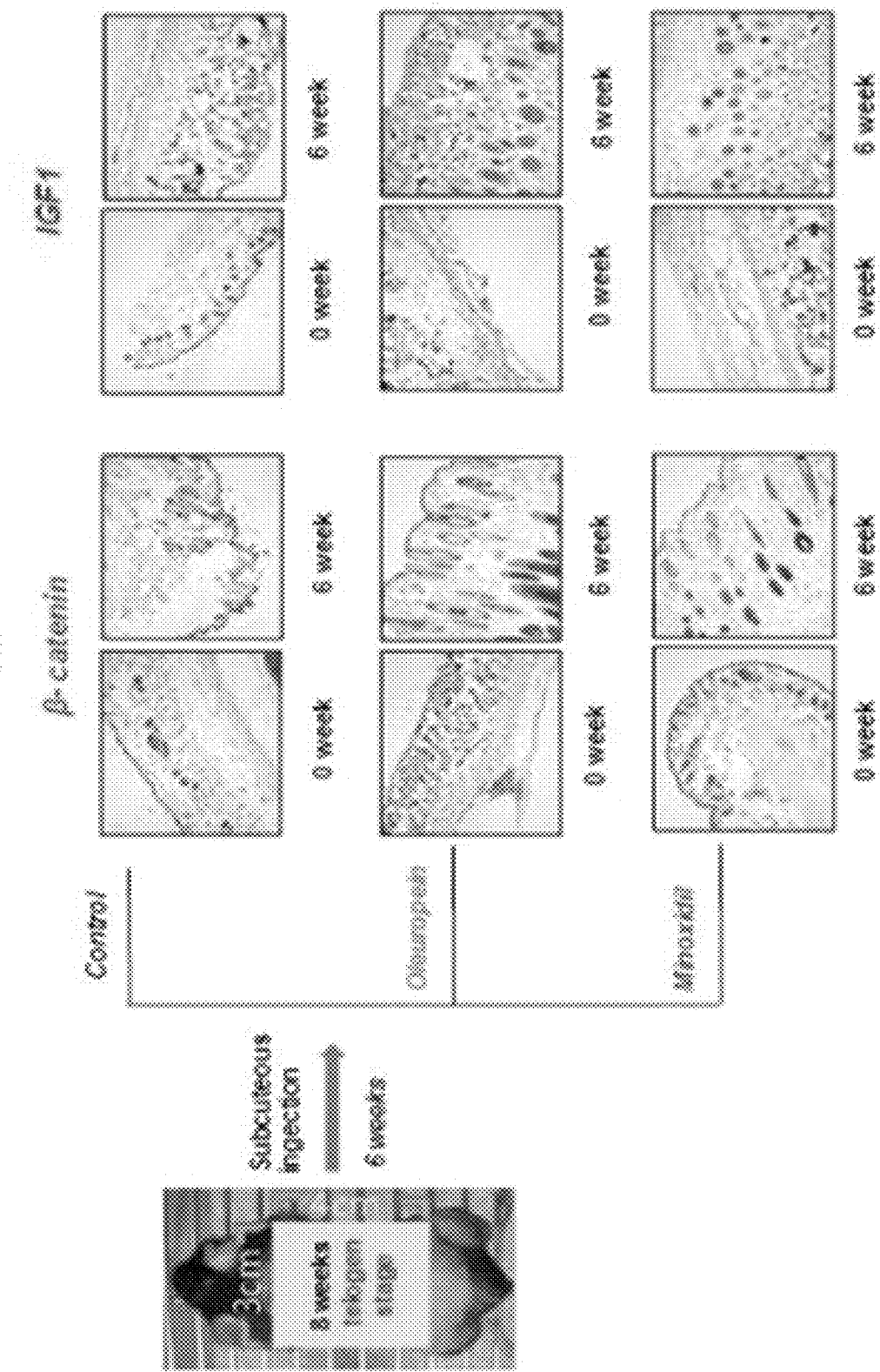
FIG. 4 represents the results on expression changes of hair growth-related proteins in the back skin of mouse subcutaneously injected with hair restorer.

In order to verify changes on expressions of hair growth-related proteins by subcutaneous injection of test substances for 6 weeks in skin tissue, immunohistochemical test was carried out. To determine whether Wnt/β-catenin signaling related to simulate hair growth is activated, protein expression level of β-catenin was measured by immunohistochemical method in skin tissue. As a result, it could be observed that protein expression level of β-catenin in the Ole group was much more highly detected than that in the negative group. In addition, protein expression level of IGF1 as growth factor for stimulating hair growth was measured by immunohistochemical method in skin tissue. As a result, it could be observed that protein expression level of IGF1 in the Ole group was much more highly detected than that in the negative group. Accordingly, it would be determined that oleuropein has more excellent effect for increasing protein expression levels of β-catenin and IGF1 than that of the minoxidil (FIG. 4).

Expression Control of Hair Growth-Related Genes in Skin Tissue (1) RNA Extraction After adding 1 mL of Trizol agent to 50-100 mg of test animal skin tissues, the mixture was homogenized and centrifuged at 12,000×g for 10 min at 4° C. The supernatant was transferred to a new tube to remove fat layer. Then, 200 μl of chloroform was added to the tube, followed by vortexing. The same procedure was repeated twice and then the supernatant was transferred to a new tube, followed by addition of isopropanol and the supernatant at 1:1 ratio. The mixture was vigorously shaken 10 times and then incubated for 10 min at room temperature, followed by centrifugation at 12,000×g for 10 min at 4° C. to remove the supernatant. After adding 1 mL of 70% ethanol to the remaining pellet, it was centrifuged at 7,500×g for 5 min at 4° C. After removing the ethanol, the RNA pellet contained in the tube was dried for 5 min at 4° C. and dissolved in nuclease-free water. The RNA sample concentration was measured at a wavelength of 260 nm and 280 nm using a UV/VIS spectrophotometer (Beckman coulter, DU730) and the integrity of RNA sample was verified by agarose gel electrophoresis.

(1) RT-PCR (Reverse Transcription-Polymerase Chain Reaction) Method

The RNA sample obtained was trasnscribed using oligo dT primer and SuperScript reverse transcriptase (GIBCO BRL, Gaithersburg, Md., USA) to synthesize cDNA. The PCR amplification was performed using the cDNA as templates and primers complementary to cDNA 5' and 3' flanking sequence. The primers were synthesized by Bioneer Inc. to use and the sequences of the primers used are presented in Table 2.

PCR reaction was conducted in the final volume of 50 μL containing 5 μL of 10× reaction buffer solution[100 mM KCL, 20 mM Tris-HCL (pH 8.0), 2.5 mM $MgCl_2$], 4 μL of 10 mM dNTP, each 1 μL of 0.2 μM sense and antisense primer, 2 μL of cDNA, 2.5 unit of Tag polymerase (Takara, Japan) and distilled water. The PCR condition was set for 4 min at 95° C., 30 sec at 94° C., 30 cycles of 30 sec at 52° C. and 45 sec at 72° C., and 10 min at 72° C. 1 μL of the amplified product was resolved on agarose gel electrophoresis.

TABLE 2

Primer sequences used for RT-PCR

| Gene | Primer | Sequence (5' → 3') | Annealing Temp (° C.) | PCR product (bp) |
|---|---|---|---|---|
| Wigless related MMTV integration site 10b (Wnt10b) | forward primer reverse primer | TTTTGGCCACTCCTCTTCCT (SEQ ID NO: 1) TCCTTTTCCAACCGAAAACC (SEQ ID NO: 2) | 61 | 183 |
| frizzled receptor 1 (FZD1) | forward primer reverse primer | TTCTATGAACAGGCCTTTCGTTCT (SEQ ID NO: 3) CCTCGTGTAGAACTTCCTCC (SEQ ID NO: 4) | 55 | 484 |

TABLE 2-continued

Primer sequences used for RT-PCR

| Gene | Primer | Sequence (5' → 3') | Annealing Temp (° C.) | PCR product (bp) |
|---|---|---|---|---|
| Low-density lipoprotein receptor-related protein 5 (LRP5) | forward primer reverse primer | AAGGGTCCACAAGGTCAAGG (SEQ ID NO: 5) AGAAGCACAGATGGCTGCAC (SEQ ID NO: 6) | 55 | 520 |
| Glycogen synthase kinase 3β (GSK3β) | forward primer reverse primer | TGTGTGAGGAACAGAACTCA (SEQ ID NO: 7) CCTACAGCCCTAGTCATCAG (SEQ ID NO: 8) | 48 | 244 |
| Axin | forward primer reverse primer | TGCAGAGTCCCAAAATGAATG (SEQ ID NO: 9) GAGCCTGTCCTTGTGTAC (SEQ ID NO: 10) | 55 | 108 |
| β-catenin | forward primer reverse primer | ATGGCTACTCAAGCTGAC (SEQ ID NO: 11) CAGCACTTTCAGCACTCTGC (SEQ ID NO: 12) | 55 | 298 |
| Insulin-like growth factor (IGF1) | forward primer reverse primer | TCAACAAGCCCACAGGGTAT (SEQ ID NO: 13) ACTCGTGCAGAGCAAAGGAT (SEQ ID NO: 14) | 60 | 280 |
| Hepatocyte growth factor (HGF) | forward primer reverse primer | CGAGGCCATGGTGCTATACT (SEQ ID NO: 15) ACACCAGGGTGATTGAGACC (SEQ ID NO: 16) | 54 | 290 |
| Vascular endothelial growth factor (VEGF) | forward primer reverse primer | TCTTCAAGCCATCCTGTGTG (SEQ ID NO: 17) GCGAGTCTGTGTTTTTGCAG (SEQ ID NO: 18) | 60 | 165 |
| Keratocyte growth facfor (KGF) | forward primer reverse primer | GACATGGATCCTGCCAACTT (SEQ ID NO: 19) AATTCCAACTGCCACTGTCC (SEQ ID NO: 20) | 54 | 686 |
| Glyceraldehyde-3-phosphatede-hydrogenase (GAPDH) | forward primer reverse primer | AGAACATCATCCCTGCATCC (SEQ ID NO: 21) TCCACCACCCTGTTGCTGTA (SEQ ID NO: 22) | 60 | 321 |

(3) Result on Expression Control of Hair Growth-Related Genes

In order to evaluate changes on expressions of hair growth-related genes by subcutaneous injection of test substances for 6 weeks in mouse back skin tissue, RT-PCR was carried out. To determine whether expressions of Wnt/β-catenin signaling molecules known as mechanism to simulate hair growth are changed, gene expression levels were measured. As a result, gene expression levels of Wnt10b and its receptor FZDR (frizzled receptor 1), and LRP5 (low-density lipoprotein receptor-related protein 5) in the Ole group were significantly increased as compared to the negative control group. For this reason, gene expression levels of GSK3β (glycogen synthase kinase 3β) and Axin inhibited by Wnt10b were significantly decreased as compared to the negative control group. As activation of Wnt/β-catenin signaling, gene expression level of β-catenin was significantly increased as compared to the negative control group.

Figure 5:
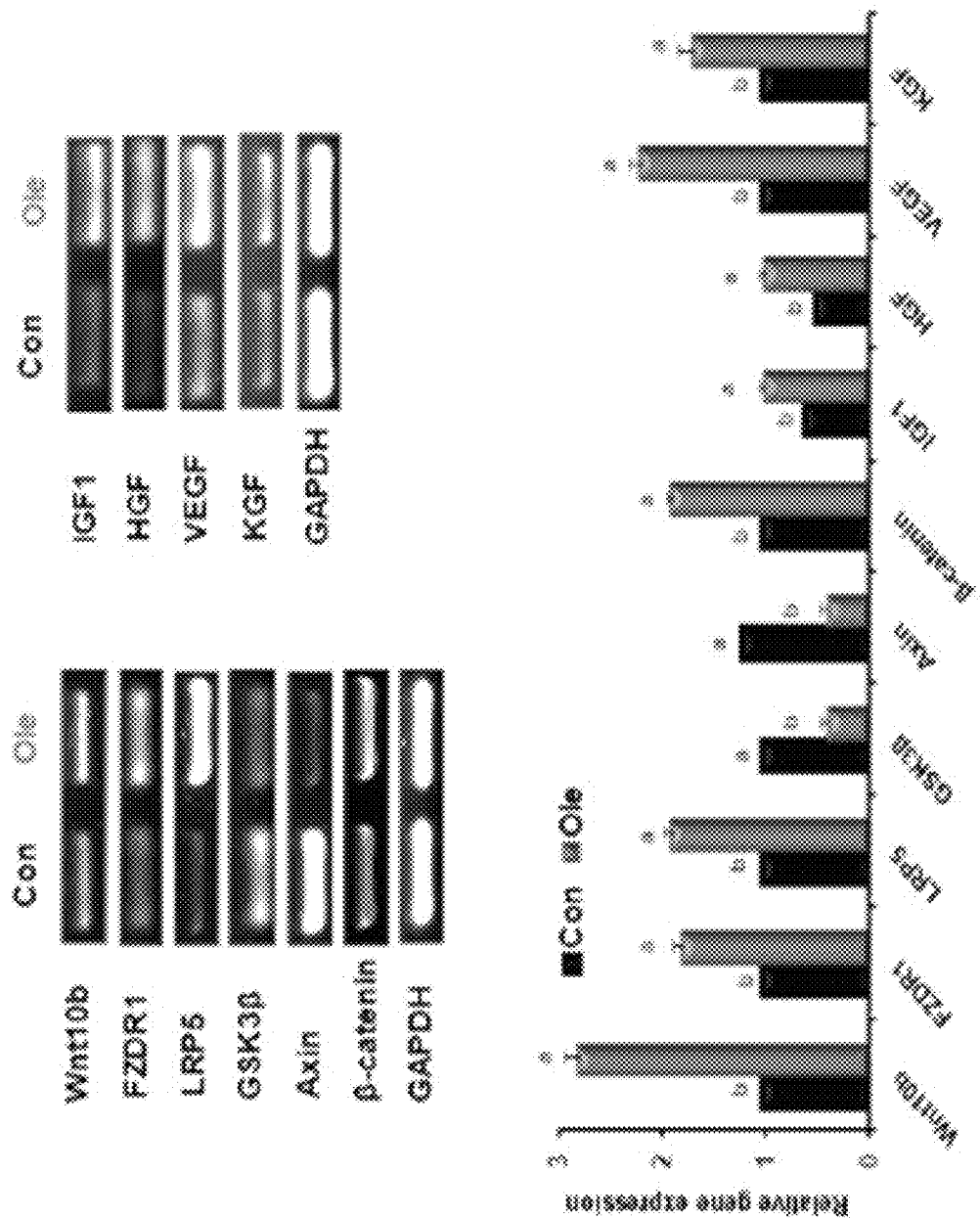
FIG. 5 represents the results on expression changes of hair growth-related genes in the back skin of mouse subcutaneously injected with hair restorer. The characters above the bars indicate significant difference among dietary groups by one-way analysis of variance (ANOVA) test and Duncan's multiple range test ($P<0.05$).

In addition, in order to verify mechanism for stimulating hair growth by oleuropein, changes on gene expressions of endocrine system factors which influence on hair growth were evaluated. Gene expression levels of IGF1 (insulin-like growth factor 1), VEGF (vascular endothelial growth factor), HGF (hepatocyte growth factor) and KGF (keratocyte growth factor) which are growth factors to influence on stimulating hair growth were measured in back skin tissues. As a result, all expression levels of these genes in the Ole group were significantly increased as compared to the negative control group (FIG. 5). Accordingly, it would be understood that oleuropein not only activates hair follicle to return to the anagen by accelerating length growth of hair follicles, but also increases expressions of IGF1, HGF, VEGF and KGF to stimulate hair re-growth.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for promoting hair growth, the method comprising:

spraying a therapeutically effective amount of a composition consisting essentially of (1) a purified secoiridoid glucoside derivative or its hydrolysate; and (2) at least one propellant selected from the group consisting of chlorofluorohydrocarbon, propane, butane, dimethyl ether, and mixtures of these propellants onto the skin of a mammalian subject in need thereof, wherein the secoiridoid glucoside derivative is represented by Chemical Formula 2:

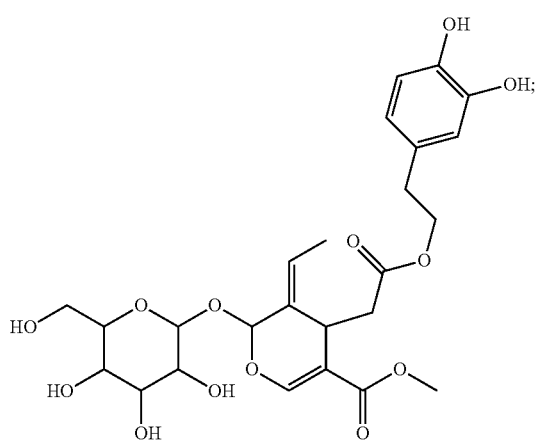

(2)

and wherein the therapeutically effective amount of the composition increases expressions of IGF-1 (Insulin-like growth factor 1), VEGF (vascular endothelial growth factor), HGF (hepatocyte growth factor), KGF (keratocyte growth factor) or β-catenin.

2. A method for promoting hair growth, the method comprising:

subcutaneously injecting a therapeutically effective amount of a composition into a mammalian subject in need thereof, wherein the composition consists essentially of a purified secoiridoid glucoside derivative or its hydrolysate and a pharmaceutically acceptable carrier, wherein the secoiridoid glucoside derivative is represented by Chemical Formula 2:

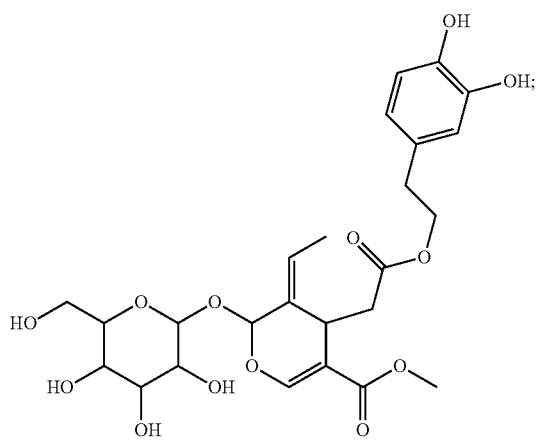

and wherein the therapeutically effective amount of the composition increases expressions of IGF-1 (Insulin-like growth factor 1), VEGF (vascular endothelial growth factor), HGF (hepatocyte growth factor), KGF (keratocyte growth factor) or β-catenin.

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: forward primer for RT-PCR (Wigless related MMTV
      integration site 10b (Wnt10b))

<400> SEQUENCE: 1
ttttggccac tcctcttcct                                                  20

<210> SEQ ID NO 2
<211> LENGTH: 20
<212> TYPE: DNA
<213> ORGANISM: Artificial Sequence
<220> FEATURE:
<223> OTHER INFORMATION: reverse primer for RT-PCR (Wigless related MMTV
      integration site 10b (Wnt10b))

<400> SEQUENCE: 2 tcctttttcca accgaaaacc                                                 20

<210> SEQ ID NO 3
<211> LENGTH: 24
<212> TYPE: DNA
<213> ORGANISM: Artificial Sequence
<220> FEATURE:
<223> OTHER INFORMATION: forward primer for RT-PCR (frizzled receptor 1
      (FZD1))

<400> SEQUENCE: 3
ttctatgaac aggcctttcg ttct                                             24

<210> SEQ ID NO 4
<211> LENGTH: 20
<212> TYPE: DNA
<213> ORGANISM: Artificial Sequence
<220> FEATURE:
<223> OTHER INFORMATION: reverse primer for RT-PCR (frizzled receptor 1
      (FZD1))

<400> SEQUENCE: 4
cctcgtgtag aacttcctcc                                                  20

<210> SEQ ID NO 5
<211> LENGTH: 20
<212> TYPE: DNA
<213> ORGANISM: Artificial Sequence
<220> FEATURE:
<223> OTHER INFORMATION: forward primer for RT-PCR (Low-density
      lipoprotein receptor-related protein 5 (LRP5))

<400> SEQUENCE: 5
aagggtccac aaggtcaagg                                                  20

<210> SEQ ID NO 6
<211> LENGTH: 20
<212> TYPE: DNA
<213> ORGANISM: Artificial Sequence
<220> FEATURE:
<223> OTHER INFORMATION: reverse primer for RT-PCR (Low-density
      lipoprotein receptor-related protein 5 (LRP5))

<400> SEQUENCE: 6
agaagcacag atggctgcac                                                  20

```
<210> SEQ ID NO 7
<211> LENGTH: 20
<212> TYPE: DNA
<213> ORGANISM: Artificial Sequence
<220> FEATURE:
<223> OTHER INFORMATION: forward primer for RT-PCR (Glycogen synthase
      kinase 3beta(GSK3beta))

<400> SEQUENCE: 7
tgtgtgagga acagaactca                                                   20

<210> SEQ ID NO 8
<211> LENGTH: 20
<212> TYPE: DNA
<213> ORGANISM: Artificial Sequence
<220> FEATURE:
<223> OTHER INFORMATION: reverse primer for RT-PCR (Glycogen synthase
      kinase 3beta(GSK3beta))

<400> SEQUENCE: 8
cctacagccc tagtcatcag                                                   20

<210> SEQ ID NO 9
<211> LENGTH: 21
<212> TYPE: DNA
<213> ORGANISM: Artificial Sequence
<220> FEATURE:
<223> OTHER INFORMATION: forward primer for RT-PCR (Axin)

<400> SEQUENCE: 9
tgcagagtcc caaaatgaat g                                                 21

<210> SEQ ID NO 10
<211> LENGTH: 18
<212> TYPE: DNA
<213> ORGANISM: Artificial Sequence
<220> FEATURE:
<223> OTHER INFORMATION: reverse primer for RT-PCR (Axin)

<400> SEQUENCE: 10
gagcctgtcc ttgtgtac                                                     18

<210> SEQ ID NO 11
<211> LENGTH: 18
<212> TYPE: DNA
<213> ORGANISM: Artificial Sequence
<220> FEATURE:
<223> OTHER INFORMATION: forward primer for RT-PCR (beta-catenin)

<400> SEQUENCE: 11
atggctactc aagctgac                                                     18

<210> SEQ ID NO 12
<211> LENGTH: 20
<212> TYPE: DNA
<213> ORGANISM: Artificial Sequence
<220> FEATURE:
<223> OTHER INFORMATION: reverse primer for RT-PCR (beta-catenin)

<400> SEQUENCE: 12
cagcactttc agcactctgc                                                   20

<210> SEQ ID NO 13
<211> LENGTH: 20
<212> TYPE: DNA
<213> ORGANISM: Artificial Sequence
```

```
<220> FEATURE:
<223> OTHER INFORMATION: forward primer for RT-PCR (Insulin-like growth
      factor(IGF1))

<400> SEQUENCE: 13
tcaacaagcc cacagggtat                                                20

<210> SEQ ID NO 14
<211> LENGTH: 20
<212> TYPE: DNA
<213> ORGANISM: Artificial Sequence
<220> FEATURE:
<223> OTHER INFORMATION: reverse primer for RT-PCR (Insulin-like growth
      factor(IGF1))

<400> SEQUENCE: 14
actcgtgcag agcaaaggat                                                20

<210> SEQ ID NO 15
<211> LENGTH: 20
<212> TYPE: DNA
<213> ORGANISM: Artificial Sequence
<220> FEATURE:
<223> OTHER INFORMATION: forward primer for RT-PCR (Hepatocyte growth
      factor (HGF))

<400> SEQUENCE: 15
cgaggccatg gtgctatact                                                20

<210> SEQ ID NO 16
<211> LENGTH: 20
<212> TYPE: DNA
<213> ORGANISM: Artificial Sequence
<220> FEATURE:
<223> OTHER INFORMATION: reverse primer for RT-PCR (Hepatocyte growth
      factor (HGF))

<400> SEQUENCE: 16
acaccagggt gattgagacc                                                20

<210> SEQ ID NO 17
<211> LENGTH: 20
<212> TYPE: DNA
<213> ORGANISM: Artificial Sequence
<220> FEATURE:
<223> OTHER INFORMATION: forward primer for RT-PCR (Vascular endothelial
      growth factor(VEGF))

<400> SEQUENCE: 17
tcttcaagcc atcctgtgtg                                                20

<210> SEQ ID NO 18
<211> LENGTH: 20
<212> TYPE: DNA
<213> ORGANISM: Artificial Sequence
<220> FEATURE:
<223> OTHER INFORMATION: reverse primer for RT-PCR (Vascular endothelial
      growth factor(VEGF))

<400> SEQUENCE: 18
gcgagtctgt gtttttgcag                                                20
```

```
<210> SEQ ID NO 19
<211> LENGTH: 20
<212> TYPE: DNA
<213> ORGANISM: Artificial Sequence
<220> FEATURE:
<223> OTHER INFORMATION: forward primer for RT-PCR (Keratocyte growth
      factor (KGF))

<400> SEQUENCE: 19
gacatggatc ctgccaactt                                              20

<210> SEQ ID NO 20
<211> LENGTH: 20
<212> TYPE: DNA
<213> ORGANISM: Artificial Sequence
<220> FEATURE:
<223> OTHER INFORMATION: reverse primer for RT-PCR (Keratocyte growth
      factor (KGF))

<400> SEQUENCE: 20
aattccaact gccactgtcc                                              20

<210> SEQ ID NO 21
<211> LENGTH: 20
<212> TYPE: DNA
<213> ORGANISM: Artificial Sequence
<220> FEATURE:
<223> OTHER INFORMATION: forward primer for RT-PCR
      (Glyceraldehyde-3-phosphatedehydrogenase (GAPDH))

<400> SEQUENCE: 21
agaacatcat ccctgcatcc                                              20

<210> SEQ ID NO 22
<211> LENGTH: 20
<212> TYPE: DNA
<213> ORGANISM: Artificial Sequence
<220> FEATURE:
<223> OTHER INFORMATION: reverse primer for RT-PCR
      (Glyceraldehyde-3-phosphatedehydrogenase (GAPDH))

<400> SEQUENCE: 22
tccaccaccc tgttgctgta                                              20
```